US007435868B2

(12) United States Patent
Hoppe et al.

(10) Patent No.: US 7,435,868 B2
(45) Date of Patent: Oct. 14, 2008

(54) **SCREENING ASSAY BASED ON THE FORKHEAD TRANSCRIPTION FACTOR-DEPENDENT *SOD-3* PROMOTER**

(75) Inventors: Edmund Hoppe, Krailling (DE); Ulrike Siebers, Munich (DE); Heike Schauerte, Munich (DE); Jonathan Rothblatt, Munich (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 638 days.

(21) Appl. No.: 10/766,339

(22) Filed: Jan. 28, 2004

(65) Prior Publication Data

US 2004/0259117 A1 Dec. 23, 2004

Related U.S. Application Data

(60) Provisional application No. 60/478,244, filed on Jun. 13, 2003.

(30) Foreign Application Priority Data

Jan. 30, 2003 (DE) ................................ 103 03 850

(51) Int. Cl.
*C12Q 1/68* (2006.01)
(52) U.S. Cl. .......................... 800/3; 800/13; 435/320.1; 435/6; 536/24.1
(58) Field of Classification Search ....................... None
See application file for complete search history.

(56) References Cited

U.S. PATENT DOCUMENTS

| 6,207,148 B1 | 3/2001 | Bandman | |
|---|---|---|---|
| 2004/0073956 A1* | 4/2004 | Verwaerde et al. .............. | 800/3 |

FOREIGN PATENT DOCUMENTS

| DE | 198 19 889 | 11/1999 |
|---|---|---|
| WO | WO 99/57314 | 11/1999 |
| WO | WO 01/18549 | 3/2001 |
| WO | WO 01/93669 | 12/2001 |
| WO | WO 01/94627 | 12/2001 |
| WO | WO 03/000861 | 1/2003 |

OTHER PUBLICATIONS

Braeckman, Bart P. et al., Insulin-like signaling, metabolism, stress resistance and aging in Caenorhabditis elegans, Mechanisms of Aging and Development, (2001), vol. 122, pp. 673-693.
Burgering, Boudewijn M. T. et al., Cell cycle and death control: long live Forkheads, Trends in Biochemical Sciences, (2002), vol. 27, No. 7, pp. 352-360.
Epstein, Henry F., Caenorhabditis elegans: Modern Biological Analysis of an Organism, Methods in Cell Biology, (1995), vol. 48, pp. 449-482.

Furuyama, Tatsuo et al., Identification of the differential distribution patterns of mRNAs and consensus binding sequences for mouse DAF-16 homologues, Biochemical Journal, (2000), vol. 349, pp. 629-634.
Gems, David et al., Two Pleiotropic Classes of daf-2 Mutation Affect Larval Arrest, Adult Behavior, Reproduction and Longetivity in Caenorhabditis elegans, Genetics, (1998), vol. 150, pp. 129-155.
Gottlieb, Shoshanna et al., daf-2, daf-16, and daf-23: Genetically Interacting Genes Controlling Dauer Formation in Caenorhabditis elegans, Genetics, (1994), vol. 137, pp. 107-120.
Hill, Stephen J. et al., Reporter-gene systems for the study of G-protein-coupled receptors, Current Opinion in Pharmacology, (2001), vol. 1, pp. 526-532.
Honda, Yoko et al., The daf-2 gene network for longevity regulates oxidative stress resistance and Mn-superoxide dismutase gene expression in Caenorhabditis elegans, FASEB Journal, (1999), vol. 13, pp. 1385-1393.
Hunter, Theresa et al., Cloning, Expression, and Characterization of Two Manganese Superoxide Dismutases from Caenorhabditis elegans, The Journal of Biological Chemistry, (1997), vol. 272, No. 45, pp. 28652-28659.
Kaestner, Klaus H. et al., Unified nomenclature for the winged helix/forkhead transcription factors, Genes & Development, (2000), vol. 14, pp. 142-146.
Manuel J. Munoz et al., Positive Selection of Caenorhabditis elegans Mutants With Increased Stress Resistance and Longevity, Genetics, (2003), vol. 163, pp. 171-180.
Riddle, Donald L. et al., Genetic and Environmental Regulation of Dauer Larva Development, C. Elegans II, (1997), Cold Harbor Springs Laboratory, pp. 739-768.
Riddle, Donald L. et al., Interacting genes in nematode dauer larva formation, Nature, (1981), vol. 290, pp. 668-669.
Sulston, John et al., Isolation of Nucleic Acids, The Nematode Caenorhabditis Elegans, (1998), Cold Spring Harbor Laboratory, pp. 604-605.
Tawe, Wilson et al., Onchocerca volvulus Superoxide Dismutase Genes: Identification of Functional Promoters for Pre-mRNA Transcripts Which Undergo trans-Splicing, Experimental Parasitology, (2000), vol. 94, pp. 172-179.
Wolfram, Markus, Reach-Through Claims und Reach-Through Licensing—Wie weit kann Patentschutz auf biotechnologische Research Tools reichen, Mittelungen der deutschen Patentanwaite, (2003), vol. 2, pp. 57-64.
Caenorhabditis elegans cosmid C08A9, PubMed No. 9851916—Medline No. 99069613, 1998.

* cited by examiner

*Primary Examiner*—James Ketter
(74) *Attorney, Agent, or Firm*—Ann Marie Szezepanik

(57) ABSTRACT

The invention relates to the identification and use of the DAF-2/IR responsive sod-3 promoter. Transgenic *C. elegans* containing sod-3 reporter gene constructs are described which are useful for, among other things, the identification of genes or compounds capable of modulating the DAF-2/IR-akt pathway. Conditions are disclosed that increase or decrease the reporter activity, demonstrating the presence of either activators or inhibitors of the DAF-2/IR pathway.

32 Claims, No Drawings

SEQUENCE LISTING

```
<160> NUMBER OF SEQ ID NOS: 3

<210> SEQ ID NO 1
<211> LENGTH: 1104
<212> TYPE: DNA
<213> ORGANISM: Caenorhabditis elegans

<400> SEQUENCE: 1
aagcttaaaa atagcagaat ttgcaaaacg agcaggaaag tcatattcgc agaaaaaagt      60
cgttgcaaac attcgttttt atatgttttt ctttgagaaa gcgtggttca tttttgaaag     120
tgaaaaatat ttgcttaaaa cttccaaatt taaatctgca gtgattcaga gaggttgaga     180
attattttca aaaacattca atgttttccc ttggagtgac tatgcaaata tgaaaatgtt     240
ttccaaaaat atttggatgc cctgataaaa agtaggtgaa atttcgcagg ggaacatcat     300
attaaaatgt tgaattttta gaagaaatgg aaatgtttgt cggtggtatg ctcgaatatt     360
tgagatatta tatatttact gttaaatccg aaattttttga caaacggaaa aaatttgtgt     420
cgaaatacta cattttcgat aacacaaagg tacttccata acacttataa aaactgtttg     480
actatcttat ttcaggaaaa aaaaatccaa gaataaacat ttttcagaat ttgaactttc     540
taatggctga ttaataaaac aaagttatac aactattcaa agcagttgct caatctggca     600
ttttcttgtg ttttttttg aatatttcat cagcaagatg ttgataattt tgtgttaatt     660
ctaattgttt tctacaattt ttcaaaccga aaattgacct ttgactttgt ttactttgtt     720
ctcgtgggtt aactgttcac tgatttctat tgctgttgat gaggtctttg atcaaatttg     780
tattgttttt atactgcata ttgcttcaat tctaaatcat ctaatatatt gtcaaacaac     840
ttcttgtttt ttttcattc aaaacttctg caaaaacgtt ctcttaacaa aggttcacac     900
aacaactctc ctctccatct ctttctctca acaacaatgt gctggccttg catgtttgcc     960
agtgcgggtt gtttacgcgt tttcaagatt tttggtctcc tatctaacgt cccgaaatgc    1020 atttttcct ttcatttggt tttttctgt tcgagaaaag tgaccgtttg tcaaatcttc    1080
```

-continued

```
taattttcag tgaataaagg atcc                                          1104

<210> SEQ ID NO 2
<211> LENGTH: 26
<212> TYPE: DNA
<213> ORGANISM: Artificial Sequence
<220> FEATURE:
<223> OTHER INFORMATION: Primer

<400> SEQUENCE: 2
agttttaaag attttattca tagtcc                                        26

<210> SEQ ID NO 3
<211> LENGTH: 31
<212> TYPE: DNA
<213> ORGANISM: Artificial Sequence
<220> FEATURE:
<223> OTHER INFORMATION: Primer

<400> SEQUENCE: 3
ggatccttta ttcactgaaa attagaagat t                                  31
```

SCREENING ASSAY BASED ON THE FORKHEAD TRANSCRIPTION FACTOR-DEPENDENT SOD-3 PROMOTER

FIELD OF THE INVENTION

The present invention relates to a process for the screening and identification of compounds modulating directly or indirectly the FOXO forkhead transcription factor activity ("FOXO activity"), transgenic C. elegans suitable for the said process, the compounds identified by the said process which modulate the FOXO activity, the use of such compounds for the treatment of disorders and the preparation of pharmaceuticals.

BACKGROUND OF THE INVENTION

In abundant food, C. elegans develops through four distinct larval stages (L1-L4) to the adulthood. However, when conditions become less favorable, the development is arrested and an alternative third-stage larvae is formed which is specialized for dispersal and long-term survival, termed dauer. Dauer larvae don't feed, are long-lived and resistant to stress. Morphologically, they can be distinguished from adults because they are thinner, darker, and have a constricted pharynx. The changes in morphology correlate with dramatic alterations in the expression pattern of genes in dauers and adults. (Riddle, 1988; Riddle and Albert, 1997)

In the past, temperature-sensitive strains have been identified that are dauer-constitutive; e.g., at the restrictive temperature of 25° C. these strains form dauers even in the presence of food (Gems, 1998). It turns out that many of these strains, termed daf strains, have acquired mutations in genes involved in the nematode insulin/IGF-1 signaling pathway. Studies of the phenotypes have allowed certain daf genes to be ordered into a genetic pathway consisting of DAF-2/IR, age-1/PI-3 Kinase, pdk-1, akt-1, akt-2, and the FOXO transcription factor DAF-16 (Gottlieb and Ruvkun, 1994; Riddle, 1977; Riddle et al, 1981, Kaestner et al., 2000).

It has been shown by Northern blotting and RT-PCR that the expression of the sod-3 gene is regulated by mutations in the DAF-2/insulin receptor pathway (Honda & Honda, 1999). Inactivation of the DAF-2 function in certain mutant strains results in a strong up-regulation of the sod-3 expression. Honda & Honda suggested that DAF-16 is the transcription factor activating the sod-3 gene and that DAF-16 is inhibited by the DAF-2/IR pathway.

Furthermore, a consensus sequence binding to the transcription factor DAF-16 has been identified and this sequence was shown to be present in the sod-3 upstream regulatory region (Furuyama et al., 2000). This binding motif fused to a minimal promoter was sufficient for insulin-regulated expression in mammalian tissue culture systems.

Since the DAF-2/insulin receptor pathway and its components are very well conserved in man, it was proposed to use the dauer phenotype to identify modulators of the insulin/IGF-1 signaling in man (WO 98/51351 A1). However, the assay systems according to the prior art require long incubation times until the developmental program of the dauer larvae has been completed (usually 3-5 days). Such a long time period may result in the degradation of the assay components. Moreover, the impermeable cuticula structure of dauers together with the reduced food-intake might be a setback for compound uptake into the worm.

Therefore, it was the underlying problem of instant invention to provide a process for the identification of compounds that modulate the DAF-2/IR pathway, which does not depend on C. elegans dauer larvae and overcomes the above-mentioned disadvantages. The process of the invention (i.e., the assay system of the invention) relies on a data read-out that is directly linked to the DAF-2/IR pathway, and which is not influenced by the progress of developmental stages of the organism under investigation, preferably mammalian and nematode cells, particularly nematode cells, e.g., C. elegans. Furthermore, the assay should provide quantitative data read-out after a short incubation time, preferably within about 8-12 hours, in the presence of the compound(s) to be investigated. Depending on the reporter used in the assay, a quantitative data read-out is obtainable in contrast to the prior art assay systems.

DETAILED DESCRIPTION OF THE INVENTION

It was found by the instant invention that the use of a nucleic acid molecule having the biological activity of an sod-3 gene promoter element surprisingly is of great advantage for the identification of genes or compounds that modulate the activity of the DAF-2/IR pathway, e.g., the sod-3 promoter as deposited at the Deutsche Sammlung für Zellkulturen und Mikroorganismen, Mascheroder Weg 1b, D-38124 Braunschweig, Germany, DSMZ No. 14912 (the 1098 bp fragment after endonuclease digestion with HindIII and BamHI) on Apr. 4, 2002, especially the sod-3 promoter according to Seq. ID No. 1. This regulatory DNA fragment contains the binding site for the FOXO DAF-16 that is functionally linked to the DAF-2/IR pathway via akt-1. In spite of current knowledge of the daf2/IR signaling pathway, a suitable responsive promoter element to monitor signaling activity for C. elegans has not been known in the art. When the sod-3 promoter is fused to reporter genes, rapid quantification of the DAF-2/IR activity can be achieved. The instant invention provides thereby the great advantage that quantification of the DAF-2/IR activity is independent of strain background or developmental stages of the C. elegans, which—according to the prior art—had to be synchronized.

Accordingly, one embodiment of the present invention is an isolated nucleic acid molecule comprising a promoter exhibiting the biological activity of the sod-3 promoter. Preferably, the nucleic acid sequence of the invention is selected from the group consisting of: (a) a nucleic acid sequence comprising the nucleic acid sequence of SEQ ID NO. 1; (b) a nucleic acid sequence that has 80%, 90%, 95% or greater sequence identity to the nucleic acid sequence of (a) having sod-3 promoter activity; (c) a fragment of the nucleic acid sequence of (a) or (b) having sod-3 promoter activity; and (d) a derivative of the nucleic acid sequence of (a), (b) or (c) having sod-3 promoter activity, preferably a DNA or RNA molecule, more preferably having a 80%, 90%, 95%, or greater sequence identity to SEQ ID No. 1; and (e) a nucleic acid sequence that hybridizes, preferably under stringent conditions, to SEQ ID NO:1. A still more preferred embodiment of the nucleic acid molecule according to the invention comprises a promoter exhibiting the biological activity of the sod-3 promoter in nematodes, preferably in *C. elegans.*

According to instant invention, a promoter exhibiting the biological activity of the sod-3 promoter means any promoter, which is responsive to forkhead transcription factors, preferably, the FOXO forkhead transcription factors (hereinafter "FOXO's"), particularly, DAF-16. Such promoters are, e.g., FOXO1a, FOXO3a or FOXO4 responsive promoters" (Kaestner et al, 2000).

According to the instant invention the term "fragment" means any parts of the nucleic acid molecules of the invention, which are long enough in order to exhibit the biological activity of the sod-3 promoter.

According to the instant invention the term "derivative" means that the sequence may differ from the sequences of the nucleic acid molecules of the invention at one or more positions, exhibiting a high degree of homology to these sequences. Hereby, "homology" means a sequence identity of at least 50 %, in particular an identity of at least 60%, preferably of more than 80 % and still more preferably a sequence identity of more than 90 %. The deviations with respect to the above-described nucleic acid molecule might have been caused by deletion, substitution, insertion or recombination. Moreover, homology means a functional and/or structural equivalence.

The invention further encompasses nucleic acid sequences that hybridize to nucleic acid sequence of SEQ ID NO:1. A nucleic acid molecule is "hybridizable" to another nucleic acid molecule, such as a cDNA, genomic DNA, or RNA, when a single stranded form of the nucleic acid molecule can anneal to another nucleic acid molecule under the appropriate conditions of temperature and solution ionic strength. The conditions of temperature and ionic strength determine the "stringency" of the hybridization. Low stringency hybridization conditions correspond to a $T_m$ of 55° C. (e.g., 5 ×sodium chloride/sodium citrate (SSC), 0.1 % SDS, 0.25 % milk, and no formamide; or 30% formamide, 5 ×SSC, 0.5% SDS). Moderate stringency hybridization conditions correspond to a higher $T_m$, (e.g., 40% formamide, with 5× or 6×SSC). High stringency hybridization conditions correspond to the highest $T_m$, (e.g., 50 % formamide, 5× or 6 ×SSC). Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of $T_m$ for hybrids of nucleic acids having those sequences. The relative stability (corresponding to higher $T_m$) of nucleic acid hybridizations decreases in the following order: RNA:RNA, DNA:RNA, DNA:DNA. For hybrids of greater than 100 nucleotides in length, equations for calculating $T_m$ have been derived. For hybridization with shorter nucleic acids, i.e., oligonucleotides, the position of mismatches becomes more important, and the length of the oligonucleotide determines its specificity.

In a particular embodiment of the present invention, a hybridizable nucleic acid molecule of the invention hybridizes under stringent conditions to the nucleic acid molecule comprising the nucleotide sequence of SEQ ID NO:1, a complement thereof, or a fragment thereof. The term "hybridizes under stringent conditions" is describes conditions for hybridization and washing under which nucleotide sequences at least 55 %, 60 %, 65 %, 70 % and preferably 75 % or more complementary to each other typically remain hybridized. Such stringent conditions are known to those skilled in the art and can be found in "Current Protocols in Molecular Biology", John Wiley & Sons, N.Y. (1989), 6.3.1-6.3.6. A preferred example of stringent hybridization conditions are hybridization in 6×SSC at about 45° C., followed by one or more washes in 0.2 ×SSC, 0.1 % SDS at 50-65 ° C.

Another embodiments of instant invention are isolated nucleic acid molecules comprising the said nucleic acid sequence according to the invention exhibiting sod-3 promoter activity and a nucleic acid sequence conferring the activity of a reporter gene ("fusion molecule"); vectors comprising the nucleic acid molecules according to the invention, which may further be optionally linked to regulatory elements which ensure the transcription and the synthesis of a translatable RNA of a reporter gene in eukaryotic cells or transgenic host cells transformed with the nucleic acid molecule or the vector of instant invention.

Still another embodiment of the invention is the transgenic host or host cell transfected with the nucleic acid molecule or the vector of the invention, which is preferably of nematode origin and the method for their preparation comprising the steps of generating a transgenic host cell, preferably of nematode origin, by use of the nucleic acid molecule or the vector of the invention.

Yet another embodiment of the present invention is a process for the identification of modulators of the DAF-2/IR pathway, AKT pathway and/or of kinases phosphorylating one or more FOXO's (i.e. the "Screening Assay" according to the invention) comprising the said transgenic cell or transgenic organism, preferably a nematode (e.g., *C. elegans*), according to the invention.

A preferred embodiment of the invention is a process for the identification of modulators of the DAF-2/IR pathway, AKT pathway, of kinases phosphorylating, phosphatases dephosphorylating, and/or other activities (e.g., enzymes) altering the molecular composition, stability (i.e., half-life), subcellular location, or activity of one or more FOXO's comprising (a) bringing transgenic *C. elegans,* preferably L1 larvae, into contact with one or more compounds to be tested for the ability to modulate the DAF-2/IR pathway, AKT pathway, of kinases phosphorylating, phosphatases dephosphorylating, and/or other activities (e.g., enzymes) altering the molecular composition, stability (i.e., half-life), subcellular location, or activity of one or more FOXO's under suitable conditions, said transgenic *C. elegans*, preferably L1 larvae, comprising the nucleic acid molecule of the invention fused to a reporter gene or the vector of the invention comprising said fusion molecule;

(b) measuring the reporter gene activity in the presence of one or more compounds to be tested;

(c) measuring the reporter gene activity in the absence of the one or more compounds to be tested, optionally in the presence of one or more suitable reference compounds;

(d) comparing the reporter gene activities of steps (b) and (c); and (e) selecting the modulating compound(s) of the DAF-2/IR pathway, AKT pathway, of kinases phosphorylating, phosphatases dephosphorylating, and/or other activities (e.g., enzymes) altering the molecular composition, stability (i.e., half-life), subcellular location, or activity of one or more FOXO's.

Another embodiment of instant invention is a process for the identification of modulators of the DAF-2/IR pathway comprising (a) bringing a transgenic *C. elegans* L1 larvae into contact with one or more compounds to be tested for the ability to modulate the DAF-2 /IR pathway under stressful condition, said L1 larvae comprising the nucleic acid molecule of the invention fused to a reporter gene or the vector of the invention comprising said fusion molecule;

(b) measuring the amount of L1 larvae, which enters into dauer larvae state under the condition of step (a) in the absence and in the presence of one or more compounds to be tested, optionally in the presence of one or more suitable reference compounds;

(c) comparing the amounts of L1 larvae, which entered into dauer larvae state according to step (b); and (d) selecting the modulating compound(s) of the DAF-2/IR pathway.

According to the instant invention the term "modulator" means any chemical molecule or genetic element, which has an inhibitory, activatory or regulatory effect on the DAF-2 /IR pathway, AKT pathway, of kinases phosphorylating, phosphatases dephosphorylating, and/or other activities (e.g., enzymes) altering the molecular composition, stability (i.e., half-life), subcellular location, or activity of one or more FOXO's.

According to the instant invention the term "suitable reference compound" means a vanadate salt, e.g., sodium orthovanadate, monoperoxo(picolinato)oxovanadate(V), or potassium bisperoxo(1,10 -phenanthroline)oxovanadate (V).

According to the instant invention the term "suitable condition" means any cultivation condition suitable for *C. elegans* known by the person skilled in the art (e.g., see Sulston & Hodgkin, 1980 ).

According to the instant invention the term "stressful condition" means any cultivation condition suitable for *C. elegans* known by the person skilled in the art, which differ from suitable conditions in that they are essentially sub-optimal without killing the worm, preferably, conditions, which are known to induce Dauer larvae formation (e.g., see Sulston & Hodgkin, 1980 ).

The Screening Assay of the invention exhibits great advantages in comparison to conventional assays (e.g., assays using exit from dauer larvae state) with respect to speed of the performance of the assay, feasibility of quantification, and avoidance of side effects, e.g., developmental side effects.

Quantifiable reporter genes suitable to practise the assay systems according to instant invention may encode for proteins that can be detected due to their enzymatic or fluorescent properties such as luciferase, β-galactosidase, β-lactamase, secreted alkaline phosphatase, green fluorescent protein, coral reef fluorescent proteins, or other reporters known to the skilled artisan (e.g., Hill et al, 2001 ). Reporter activity might be measured in lysates of the organisms or in-situ in the living cell or animal.

Activation of the reporter reveals in the identification of inhibitors of the DAF-2/IR or AKT pathway, while a down-regulation of the reporter activity is indicative for activators of the said pathway. The reporter might be used in wild-type *C. elegans* or in combination with certain strains that might contain mutations in genes associated with, for example, the dauer pathway, preferably daf-2 mutant strains.

The identified compounds, which inhibit the signaling of the DAF-2 /IR pathway components are promising candidates as therapeutic agents in the field of oncology and cardiac hypertrophy, while activators of the said pathway are promising candidates as therapeutic agents in the treatment of diabetes, brain/heart ischemia, or neurodegenerative diseases.

EXAMPLES

The following examples are not to be understood as limiting the invention but shall merely illustrate the inventive concept:

Material and Methods

Genomic DNA was prepared from wild type *C. elegans* (N2) using proteinase K and phenol extraction as described previously (Sulston and Hodgkin, 1980).

The *C. elegans* vectors pPD49.26 and pPD95.75 were used according to Fire et al. (Methods in Cell Biology, Vol. 48, Chapter 19 (C. Mello and A. Fire), Academic Press).

Example 1 Isolation of the Sod-3 Promoter

To isolate the regulatory sequences of the sod-3 gene, 1266 bp upstream of the start codon were amplified from wild type *C. elegans* (N2, Bristol, Caenorhabditis Genetics Center, 250 Biological Science Center, University of Minnesota, 1445 Gortner Avenue, St. Paul, Minn. 55108-1095, USA) genomic DNA by polymerase chain reaction with the upstream primer sod-5U (Seq. ID No. 2) and the downstream primer sod-3 U (Seq. ID No. 3 ), adding a 3 'BamHI restriction site to the PCR product. The oligonucleotide primers used were as follows:

forward sod-5U:

5'-agttttaaagattttattcatagtcc-3';   (Seq ID No. 2)

reverse sod-3D:

5'-ggatcctttattcactgaaaattagaagatt-   (Seq ID No. 3)

3'.

Subsequently, the identity of the resulting 1266 bp PCR product was confirmed by sequencing. The GFP expression vector was assembled by cloning into the pPD49.26 backbone a) the 1098 bp BamHI and HindIII fragment of the sod-3 promoter and b) and a PCR fragment of GFP amplified from pPD95.75 containing flanking restriction sites for NheI and KpnI.

The resulting in a *C. elegans* expression vector containing the sod-3::GFP fusion was termed pMGC2-24

Example 2 Transgenic *C. Elegans* daf-2(e1368) animals and transgenic animals were obtained according to a standard procedure (Mello and Fire, 1995 ). In contrast to the method of Mello and Fire, the plasmid pMGC2-24 was injected together with the injection marker ttx-3::GFP into the gonads of the said animals. Three independent lines were isolated by isolation of GFP-positive animals.

Example 3 Specific Read-Out for the DAF-2/Insulin Receptor Pathway

The regulation of the sod-3 promoter was demonstrated by comparing the expression of sod-3::GFP in daf-2 (e1368 ) animals at different temperatures. The daf-2(e1368 ) strain contains a temperature-sensitive mutation in the ligand-binding domain of DAF-2 /IR resulting in an inactivation of DAF-2 at 25 ° C. When L1 larvae were grown up at the permissive temperature of 15 ° C. for 4 days, a weak expression of GFP could be detected in the tail, head, and in the vulva of the adults animals. The overall expression of GFP was quite low. This changed dramatically when L1 larvae were grown up at the restrictive temperature of 25 ° C. with a concomitant inactivation of DAF-2. Under these conditions, the *C. elegans* were arrested as dauers and GFP fluorescence was strongly up-regulated in the whole animal. The up-regulation of sod-3::GFP was abolished in a daf-2 (e1368 ) strain which had an additional deletion in the daf-16 gene. Likewise, under these experimental conditions, wild-type N2 worms with normal DAF-2 /IR function kept at 25 ° C. neither formed dauers nor did they respond with an increase in sod-3 expression.

Therefore, the regulation of the sod-3::GFP expression correlated with the inactivation of the DAF-2/ IR pathway in the daf-2 (e1368 ) strain at 25 ° C. The data are in agreement with a model in which the DAF-2/ IR pathway acts to inhibit the transcription factor DAF-16 which otherwise activates the transcription of the sod-3 gene. Therefore, the reporter is activated when the DAF-2 /IR pathway is switched off and deactivated when the DAF-2 /IR pathway is switched on.

Example 4 The Sod-3::GFP Reporter is Regulated Independent of the Developmental Stage daf-2 (e1368 ) animals containing the sod-3::GFP reporter were kept at 15 ° C. until they finished the development to adults and were then shifted as adults to 25 ° C. (restrictive temperature) to inactivate DAF-2/ IR. As seen with dauers, also adults exposed to the restrictive temperature expressed much more GFP in comparison to animals kept at the permissive temperature of 15 ° C. Densitometric scanning revealed an increase from 2.6±1.7 mean GFP at the permissive temperature to 53.5±14.6 mean GFP at the restrictive temperature. The increase in GFP expression in the adults is in the same order of magnitude as seen with L1 shifted immediately to 25° C. to give dauers (mean GFP: 87.8±35.3). This suggests that the regulation of the sod-3 promoter is independent of the developmental stage of the *C. elegans,* and that up-regulation of the sod-3 promoter as a consequence of the inactivation of the daf-2/IR gene can be induced at any time. Consequently, the sod-3 *C. elegans* strain can be used for screening with adult *C. elegans* thus avoiding potential interference of compounds with nematode development. In addition, incubation times can be shorter since the assay is not dependent on the completion of the developmental program.

SEQ ID No:1 (sod-3 promoter (HindIII×BamHI fragment of DSMZ plasmid pMGC 2 -24). The sequence begins and ends with the restriction sites of HindIII, resp., BamHI:

```
aagcttaaaaatagcagaatttgcaaaacgagcaggaaagtcatattcgcagaaaaaagtcgttgcaaacattcgttt ttatatgttttctttgagaaagcgtggttcattttgaaagtgaaaaatatttgcttaaaacttccaaatttaaatctgcagtga ttcagagaggttgagaattattttcaaaaacattcaatgttttcccttggagtgactatgcaaatatgaaaatgttttccaaa aatatttggatgccctgataaaaagtaggtgaaatttcgcagggaacatcatattaaaatgttgaattttagaagaaat ggaaatgtttgtcggtggtatgctcgaatatttgagatattatatatttactgttaaatccgaaattttgacaaacggaaaa aatttgtgtcgaaatactacattttcgataacacaaaggtacttccataacacttataaaaactgtttgactatcttatttcag gaaaaaaaatccaagaataaacattttcagaatttgaactttctaatggctgattaataaaacaaagttatacaacta ttcaaagcagttgctcaatctggcatttcttgtgttttttttgaatatttcatcagcaagatgttgataattttgtgttaattctaat tgttttctacaattttcaaaccgaaaattgacctttgactttgtttactttgttctcgtgggttaactgttcactgatttctattgctg ttgatgaggtctttgatcaaatttgtattgtttttatactgcatattgcttcaattctaaatcatctaatatattgtcaaacaacttct tgtttttttttcattcaaaacttctgcaaaaacgttctcttaacaaaggttcacacaacaactctcctctccatctctttctctca acaacaatgtgctggccttgcatgtttgccagtgcgggttgtttacgcgttttcaagattttggtctcctatctaacgtcccg aaatgcattttttcctttcatttggttttttctgttcgagaaaagtgaccgtttgtcaaatcttctaattttcagtgaataaggat cc
```

REFERENCES

T. Furuyama, T. Nakazawa, I. Nakano, and N. Mori. Identification of the differential distribution patterns of mRNAs and consensus binding sequences for mouse DAF-16 homologues. Biochem.J. 349 (Pt 2):629-634, 2000.

D. Gems, A. J. Sutton, M. L. Sundermeyer, P. S. Albert, K. V. King, M. L. Edgley, P. L. Larsen, and D. L. Riddle. Two pleiotropic classes of DAF-2 mutation affect larval arrest, adult behavior, reproduction and longevity in *Caenorhabditis elegans*. Genetics 150 (1):129-155, 1998.

S. Gottlieb and G. Ruvkun. DAF-2, DAF-16 and DAF-23: genetically interacting genes controlling Dauer formation in *Caenorhabditis elegans*. Genetics 137 (1):107-120, 1994.

S. J. Hill, J. G. Baker, and S. Rees. Reporter-gene systems for the study of G-protein-coupled receptors. *Curr. Opin. Pharmacol*. 1 (5):526-532, 2001.

Y. Honda and S. Honda. The DAF-2 gene network for longevity regulates oxidative stress resistance and Mn-superoxide dismutase gene expression in Caenorhabditis elegans. FASEB J. 13 (11):1385-1393, 1999.

K. H. Kaestner, W. Knochel, and D. E. Martinez. Unified nomenclature for the winged helix/forkhead transcription factors. Genes Dev. 14 (2):142-146, 2000.

C. Mello and A. Fire in "*Caenorhabditis elegans*, Modern Biological Analysis of an Organism" (ed. H. F. Epstein and D. C. Shakes), pp 451-482, Methods in Cell Biology, Vol. 48, 1995 Academic Press.

D. L. Riddle. A genetic pathway for dauer larva formation in *Caenorhabditis elegans*. *Stadler Genetics Symposium* 9:101-120, 1977.

D. L. Riddle, M. M. Swanson, and P. S. Albert. Interacting genes in nematode dauer larva formation. Nature 290 (5808):668-671, 1981.

D. L. Riddle, in "The Nematode *Caenorhabditis elegans*". (ed. W. B. Wood), pp 393-412, 1988 Cold Spring Harbor Laboratory.

D. L. Riddle and Albert, in "*C. elegans* II" (ed. D. L. Riddle, T. Blumenthal, B. J. Meyer, J. R. Priess), pp.739-768, 1997 Cold Spring Harbor Laboratory.

J. Sulston and J. Hodgkin in "The Nematode *Caenorhabditis elegans*". (ed. W. B. Wood), pp 604-605, 1988 Cold Spring Harbor Laboratory.

The foregoing references, as well as all other references cited herein, are incorporated herein by reference in their entirety.

---

We claim:

1. An isolated nucleic acid molecule comprising the nucleic acid sequence of SEQ ID NO:1.

2. The isolated nucleic acid molecule of claim 1, wherein the nucleic acid molecule is selected from the group consisting of a DNA molecule and an RNA molecule.

3. An isolated nucleic acid molecule comprising a nucleic acid sequence having 90% or greater sequence identity to the nucleic acid sequence of SEQ ID NO:1 and further comprises at least one forkhead transcription factor binding site.

4. An isolated nucleic acid molecule comprising a promoter exhibiting the biological activity of the sod-3 promoter, wherein the nucleic acid sequence is
  a nucleic acid sequence that has 90% or greater sequence identity to the nucleic acid sequence of SEQ ID NO:1 and further comprises at least one forkhead transcription factor binding site.

5. An isolated nucleic acid molecule comprising the nucleic acid molecule of claim 1 and a nucleic acid sequence conferring the activity of a reporter gene.

6. An isolated nucleic acid molecule comprising the nucleic acid molecule of claim 3 and a nucleic acid sequence conferring the activity of a reporter gene.

7. A vector comprising the nucleic acid molecule of claim 1.

8. The vector of claim 7 wherein the nucleic acid molecule comprises DNA.

9. The vector of claim 8 wherein the DNA is linked to regulatory elements which ensure the transcription and the synthesis of a translatable RNA of a reporter gene in eukaryotic cells.

10. A vector comprising the nucleic acid molecule of claim 3.

11. The vector of claim 10 wherein the nucleic acid molecule comprises DNA.

12. The vector of claim 11 wherein the DNA is linked to regulatory elements which ensure the transcription and the synthesis of a translatable RNA of a reporter gene in eukaryotic cells.

13. A transgenic host cell transformed with the nucleic acid molecule of claim 1.

14. The transgenic host cell of claim 13 wherein the transgenic host cell is a nematode cell.

15. A transgenic host comprising the host cell of claim 13 wherein the transgenic host is a nematode.

16. A trausgenic host cell transformed with the nucleic acid molecule of claim 3.

17. The transgenic host cell of claim 15 wherein the transgenic host cell is a nematode cell.

18. The transgenic host of claim 17 wherein the transgenic host is a nematode.

19. A method for identifying a modulating compound, the method comprising
  (a) providing transgenic *C. elegans* comprising the nucleic acid molecule of claim 1;
  (b) contacting the transgenic *C. elegans* with at least one compound;
  (c) measuring reporter gene activity in the absence and in the presence of the at least one compound;
  (d) comparing the reporter gene activities of step (c); and
  (e) selecting thereby at least one compound.

20. The method of claim 19 wherein the *C. elegans* are L1 larvae.

21. The method of claim 19 wherein the step of measuring reporter gene activity further comprising measuring the activity in the presence of at least one reference compounds.

22. A method for identifying a modulating compound, the method comprising
  (a) providing transgenic *C. elegans* comprising the nucleic acid molecule of claim 3;
  (b) contacting the transgenic *C. elegans* with at least one compound;
  (c) measuring reporter gene activity in the absence and in the presence of the at least one compound;
  (d) comparing the reporter gene activities of step (c); and
  (e) selecting thereby at least one modulating compound.

23. The method of claim 22 wherein the *C. elegans* are L1 larvae.

24. The method of claim 22 wherein the step of measuring reporter gene activity further comprising measuring the activity in the presence of at least one reference compounds.

25. A process for identifying modulators of the DAF-2/IR pathway, the method comprising:
(a) providing transgenic *C. elegans* L1 larvae comprising the nucleic acid molecule of claim 1;
(b) contacting the transgenic *C. elegans* L1 larvae with at least one compound under stressful conditions;
(e) measuring the amount of L1 larvae in the absence and in the presence of the at least one compound;
(d) comparing the amount of L1 larvae which entered into dauer larvae state with the amount of L1 larvae which did not enter into dauer larvae state; and
(e) selecting thereby at least one modulating compound.

26. The method of claim 25 wherein the step of measuring the amount of L1 larvae further comprises measuring the amount of L1 larvae in the presence of at least one reference compound.

27. A process for identifying modulators of the DAF-2/IR pathway, the method comprising;
(a) providing transgenic *C. elegans* L1 larvae comprising the nucleic acid molecule of claim 3;
(b) contacting the transgenic *C. elegans* L1 larvae with at least one compound under stressful conditions;
(c) measuring the amount of L1 larvae in the absence and in the presence of the at least one compound;
(d) comparing the amount of L1 larvae which entered into dauer larvae state with the amount of L1 larvae which did not enter into dauer larvae state; and
(e) selecting thereby at least one modulating compound.

28. The method of claim 27 wherein the step of measuring the amount of L1 larvae further comprises measuring the amount of L1 larvae in the presence of at least one reference compound.

29. The isolated nucleic acid molecule of claim 3 wherein the forkhead transcription factor is a FOXO forkhead transcription factor.

30. The isolated nucleic acid molecule of claim 3 wherein the forkhead transcription factor is DAF-16.

31. The isolated nucleic acid molecule of claim 4 wherein the forkhead transcription factor is a FOXO forkhead transcription factor.

32. The isolated nucleic acid molecule of claim 4 wherein the forkhead transcription factor is DAF-16.

* * * * *